(12) United States Patent
VanAtta et al.

(10) Patent No.: US 6,573,048 B1
(45) Date of Patent: Jun. 3, 2003

(54) DEGRADABLE NUCLEIC ACID PROBES AND NUCLEIC ACID DETECTION METHODS

(75) Inventors: Reuel VanAtta, Mountain View, CA (US); David Albagli, Menlo Park, CA (US); Michael L. Wood, Mountain View, CA (US); Peter C. Cheng, San Jose, CA (US)

(73) Assignee: Naxcor, Mountain View, CA (US)

( * ) Notice: Subject to any disclaimer, the term of this patent is extended or adjusted under 35 U.S.C. 154(b) by 0 days.

(21) Appl. No.: 09/551,305

(22) Filed: Apr. 18, 2000

(51) Int. Cl.$^7$ ................................................. C12Q 1/68
(52) U.S. Cl. ........................... 435/6; 435/7.1; 435/91.1; 435/91.2; 536/22.1; 536/23.1
(58) Field of Search ..................... 435/6, 7.1, 91.1, 435/91.2; 536/22.1, 23.1, 24.3, 24.32, 24.33

(56) References Cited

U.S. PATENT DOCUMENTS

| | | | |
|---|---|---|---|
| 4,599,303 A | * 7/1986 | Yabusaki et al. ............... | 435/6 |
| 4,826,967 A | 5/1989 | Glass ........................... | 536/23 |
| 5,082,934 A | 1/1992 | Saba et al. ................... | 536/17.6 |
| 5,403,711 A | * 4/1995 | Walder et al. ................. | 435/6 |
| 5,616,464 A | 4/1997 | Albali et al. ................... | 435/6 |
| 5,843,650 A | * 12/1998 | Segev ........................... | 435/6 |
| 6,004,826 A | * 12/1999 | Segev ........................... | 435/6 |
| 6,005,093 A | 12/1999 | Wood et al. ................... | 536/24.3 |
| 6,124,099 A | * 9/2000 | Heckman et al. .............. | 435/6 |
| 6,177,243 B1 | * 1/2001 | Albagli et al. ................. | 435/6 |
| 6,303,799 B1 | 10/2001 | Cheng et al. .................. | 549/441 |

FOREIGN PATENT DOCUMENTS

| | | |
|---|---|---|
| WO | 97/16567 | 5/1997 |
| WO | 99/35288 | 7/1999 |
| WO | 99/42616 | 8/1999 |

OTHER PUBLICATIONS

Darnell et al., *Molecular Cell Biology*, Second Edition, Scientific American Books, Inc., (1990).
International Search Report for PCT/US01/12701 (Jul. 10, 2002).
Lehninger et al., *Principles of Biochemistry*, Second Edition, Worth Publishers, Inc. (1993).
Sambrook et al., *Molecular Cloning, A Laboratory Manual*, Second Edition, Cold Spring Harbor Laboratory Press (1989).

* cited by examiner

*Primary Examiner*—Jeffrey Siew
(74) *Attorney, Agent, or Firm*—Dorsey & Whitney LLP

(57) ABSTRACT

Nucleic acid probes that are susceptible to chemical or enzymatic degradation are described herein. In addition, assays and methods using such probes in the detection of target nucleic acid sequences are disclosed. The target-specific hybridization region or target-complementary region of the degradable probes can be separated via a degradation process from the detectable region. The remaining portion of the degradable probes can be easily detected. The use of the degradable probes described herein improves the signal-to-noise ratio by reducing background specific or non-specific signal generation in assays and methods of nucleic acid detection.

21 Claims, No Drawings

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<221> NAME/KEY: misc_feature
<222> LOCATION: (25)..(25)
<223> OTHER INFORMATION: Biotin TEG is attached to the 3' end of the sequence.
<221> NAME/KEY: source
<222> LOCATION: (1)..(25)

```
<223> OTHER INFORMATION: The artificial sequence is an oligonucleotide
      probe prepared with an automated DNA synthesis instrument.
<221> NAME/KEY: misc_feature
<222> LOCATION: (24)..(25)
<223> OTHER INFORMATION: 3-(7-coumarinyl) glycerol is inserted between
      position 24 and 25.

<400> SEQUENCE: 1
tctgccgatc catactgcgg aacaa                                        25

<210> SEQ ID NO 2
<211> LENGTH: 26
<212> TYPE: DNA
<213> ORGANISM: Artificial Sequence
<220> FEATURE:
<221> NAME/KEY: misc_feature
<222> LOCATION: (11)..(11)
<223> OTHER INFORMATION: The letter m indicates that either a or c may
      be at position 11.
<221> NAME/KEY: source
<222> LOCATION: (1)..(26)
<223> OTHER INFORMATION: The artificial sequence is an oligonucleotide
      probe prepared with an automated DNA synthesis instrument.
<221> NAME/KEY: misc_feature
<222> LOCATION: (1)..(1)
<223> OTHER INFORMATION: Fluorescein phosphoramidite and tetraethylene
      glycol are attached to the 5' end via a phosphorothioate
      diester linkage.

<400> SEQUENCE: 2
ttttcctagc mgcttgtttt gctcgc                                       26

<210> SEQ ID NO 3
<211> LENGTH: 24
<212> TYPE: DNA
<213> ORGANISM: Artificial Sequence
<220> FEATURE:
<221> NAME/KEY: misc_feature
<222> LOCATION: (24)..(24)
<223> OTHER INFORMATION: Biotin TEG is attached to the 3' end of the
      sequence.
<221> NAME/KEY: source
<222> LOCATION: (1)..(24)
<223> OTHER INFORMATION: The artificial sequence is an oligonucleotide
      probe prepared with an automated DNA synthesis instrument.
<221> NAME/KEY: misc_feature
<222> LOCATION: (23)..(24)
<223> OTHER INFORMATION: 3-(7-coumarinyl) glycerol is inserted between
      position 23 and 24.

<400> SEQUENCE: 3
tatatggatg atgtggtatt ggaa                                         24

<210> SEQ ID NO 4
<211> LENGTH: 24
<212> TYPE: DNA
<213> ORGANISM: Artificial Sequence
<220> FEATURE:
<221> NAME/KEY: misc_feature
<222> LOCATION: (20)..(20)
<223> OTHER INFORMATION: The letter r indicates that either g or a may
      be at position 20.
<221> NAME/KEY: source
<222> LOCATION: (1)..(24)
<223> OTHER INFORMATION: The artificial sequence is an oligonucleotide
      probe prepared with an automated DNA synthesis instrument.
<221> NAME/KEY: misc_feature
<222> LOCATION: (1)..(1)
<223> OTHER INFORMATION: Fluorescein phosphoramidite and tetraethylene
      glycol are attached to the 5' end via a phosphorothioate
      diester linkage.
```

```
<400> SEQUENCE: 4
tttgggccaa gtctgtacar catc                                          24

<210> SEQ ID NO 5
<211> LENGTH: 26
<212> TYPE: DNA
<213> ORGANISM: Artificial Sequence
<220> FEATURE:
<221> NAME/KEY: misc_feature
<222> LOCATION: (26)..(26)
<223> OTHER INFORMATION: Biotin TEG is attached to the 3' end of the
      sequence.
<221> NAME/KEY: source
<222> LOCATION: (1)..(26)
<223> OTHER INFORMATION: The artificial sequence is an oligonucleotide
      probe prepared with an automated DNA synthesis instrument.
<221> NAME/KEY: misc_feature
<222> LOCATION: (25)..(26)
<223> OTHER INFORMATION: 3-(7-coumarinyl) glycerol is inserted between
      position 25 and 26.
<221> NAME/KEY: misc_feature
<222> LOCATION: (19)..(19)
<223> OTHER INFORMATION: The letter y indicates that either c or t may
      be at position 19.

<400> SEQUENCE: 5
catttgttca gtggttcgya gggcaa                                        26

<210> SEQ ID NO 6
<211> LENGTH: 27
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: Fluorescein phosphoramidite and tetraethylene
      glycol are attached to the 5' end via a phophorothioate
      diester linkage.
<221> NAME/KEY: source
<222> LOCATION: (1)..(27)
<223> OTHER INFORMATION: The artificial sequence is an oligonucleotide
      probe prepared with an automated DNA synthesis instrument.

<400> SEQUENCE: 6
tttttccccc cactgtttgg ctttcag                                       27

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (25)..(25)
<223> OTHER INFORMATION: Biotin TEG is attached to the 3' end of the
      sequence.
<221> NAME/KEY: source
<222> LOCATION: (1)..(25)
<223> OTHER INFORMATION: The artificial sequence is an oligonucleotide
      probe prepared with an automated DNA synthesis instrument.
<221> NAME/KEY: misc_feature
<222> LOCATION: (24)..(25)
<223> OTHER INFORMATION: 3-(7-coumarinyl) glycerol is inserted between
      position 24 and 25.

<400> SEQUENCE: 7
cagagtctag actcgtggtg gacaa                                         25

<210> SEQ ID NO 8
<211> LENGTH: 22
<212> TYPE: DNA
```

```
<213> ORGANISM: Artificial Sequence
<220> FEATURE:
<221> NAME/KEY: misc_feature
<222> LOCATION: (1)..(1)
<223> OTHER INFORMATION: Fluorescein phosphoramidite and tetraethylene
      glycol are attached to the 5' end via a phosphorothioate
      diester linkage.
<221> NAME/KEY: source
<222> LOCATION: (1)..(22)
<223> OTHER INFORMATION: The artificial sequence is an oligonucleotide
      probe prepared with an automated DNA synthesis instrument.

<400> SEQUENCE: 8
tttttctctc aattttctag gg                                          22

<210> SEQ ID NO 9
<211> LENGTH: 27
<212> TYPE: DNA
<213> ORGANISM: Artificial Sequence
<220> FEATURE:
<221> NAME/KEY: misc_feature
<222> LOCATION: (26)..(27)
<223> OTHER INFORMATION: 3-(7-coumarinyl) glycerol is inserted between
      position 26 and 27.
<221> NAME/KEY: source
<222> LOCATION: (1)..(27)
<223> OTHER INFORMATION: The artificial sequence is an oligonucleotide
      probe prepared with an automated DNA synthesis instrument.
<221> NAME/KEY: misc_feature
<222> LOCATION: (27)..(27)
<223> OTHER INFORMATION: Biotin TEG is attached to the 3' end of the
      sequence.

<400> SEQUENCE: 9
agcgccaaaa ttcgcagtcc ccaacaa                                     27

<210> SEQ ID NO 10
<211> LENGTH: 28
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: Fuorescein phosphoramidite and tetraethylene
      glycol are attached to the 5' end via a phosphorothioate
      diester linkage.
<221> NAME/KEY: source
<222> LOCATION: (1)..(28)
<223> OTHER INFORMATION: The artificial sequence is an oligonucleotide
      probe prepared with an automated DNA synthesis instrument.

<400> SEQUENCE: 10
tttctccaat cactcaccaa cctcttgt                                    28

<210> SEQ ID NO 11
<211> LENGTH: 58
<212> TYPE: DNA
<213> ORGANISM: Artificial Sequence
<220> FEATURE:
<221> NAME/KEY: source
<222> LOCATION: (1)..(58)
<223> OTHER INFORMATION: The artificial sequence is a nucleic acid
      sequence which serves as a target sequence derived from a
      biological sample or prepared with an automated DNA synthesis
      instrument.

<400> SEQUENCE: 11
gatgctattc gcggttttaa gcgtcagggg ttggaggtta gtgagtggtt ggagaaca    58
```

DEGRADABLE NUCLEIC ACID PROBES AND NUCLEIC ACID DETECTION METHODS

BACKGROUND OF THE INVENTION a) Field of the Invention

The present invention relates to nucleic acid probes that are susceptible to chemical or enzymatic degradation and to assays and methods using such probes in the detection of target nucleic acid sequences in a sample.

b) Description of Related Art

The nucleic acids, deoxyribonucleic acid (DNA) and ribonucleic acid (RNA), are the molecular repositories for genetic information. Ultimately, every protein is the result of the information contained in the cell's nucleic acids. A gene is a segment of DNA that contains the information for a functional biological product such as a protein or RNA. The function of DNA is the storage of biological information, and since cells have typically many thousands of genes, DNA molecules tend to be very large. The total length of all DNA in a single human cell is about two meters, consisting of billions of nucleotides.

In eukaryotic organisms, DNA is largely found in the nucleus of the cell. But protein synthesis occurs on ribosomes in the cytoplasm, hence a molecule other than DNA must carry the genetic message for protein synthesis from the nucleus to the cytoplasm. RNA is found in both the nucleus and cytoplasm, and it carries genetic information from DNA to the ribosome. Several classes of RNAs exist, each having distinct function. Ribosomal RNAs (rRNA) are structural components of ribosomes that carry out the synthesis of proteins. Messenger RNAs (mRNA) are nucleic acids that carry the information from the genes to the ribosome, where the corresponding proteins are made. Transfer RNAs (tRNA) are adapter molecules that translate the information in mRNA into a specific sequence of amino acids. There are also a wide variety of special-function RNAs that carry out additional functions in the cell (Lehninger et al., *Principles of Biochemistry*, Second Edition, 1993, Worth Publishers, Inc.).

Double-helical DNA consists of two polynucleic acid strands, twisted around each other.

Each nucleotide unit of the polynucleotide strand consists of a nitrogenous base (A, T, C, or G), a sugar deoxyribose, and a phosphate group. The orientation of the two polynucleotide strands is antiparallel in that their 5' to 3' directions are opposite. The strands are held together by ydrogen bonds and hydrophobic interactions. The base pairs in DNA consist of purines such as adenine (A) and guanine (G), and pyrimidines such as thymine (T) and cytosine (C). A is paired with T by forming two hydrogen bonds while G is paired with C by forming three hydrogen bonds. This base pair complementarity is an essential feature of the DNA molecule and is due to the size, shape, and chemical composition of the bases. As a result of the geometry of the double helix, a purine must always pair with a pyrimidine. Furthermore, G will always pair with a C, and A will always pair with T. This simple and elegant structure provides for the extraordinary stability of the double helix.

Under the conditions of temperature and ion concentration found in cells, DNA is maintained as a two-stranded structure by the hydrogen bonds of the A-T and G-C base pairs. The duplexes can be melted (denatured into single strands) by heating them (usually in a dilute salt solution of, for example, 0.01 M NaCl) or by raising the pH above 11. If the temperature is lowered and the ion concentration in the solution is raised, or if the pH is lowered, the single strands will anneal, or reassociate, to reconstitute duplexes (if their concentration in solution is great enough). This property is the basis of a technique referred to as nucleic acid hybridization. In a mixture of nucleic acids, only complementary strands will reassociate; the extent of their reassociation is virtually unaffected by the presence of noncomplementary strands. The molecular hybridization can take place between complementary strands of either DNA or RNA or between an RNA strand and a DNA strand.

The use of various hybridization techniques employing oligonucleotide probes to detect genes (and RNA) of interest is well known in the art of molecular biology. Generally, probes are designed so that they hybridize to fragments containing a complementary nucleic acid sequence. The existence and amounts of hybrid formed are detected by measuring radiation (for radioactive probes), enzyme-produced products (for enzyme-labeled probes), fluorescence (for fluorescent-labled probes), and the like, depending on the nature of the signal being used. Various experimental conditions must be calculated to estimate nucleic acid duplex stability of probe-target complexes and to reduce nonspecific (background) binding of probes to non-target DNA or RNA. Due to the many variables that need to be considered when performing hybridization assays, including melting temperature or other denaturation conditions, annealing temperature, salt concentration, pH, and others, the likelihood of nonspecific binding of nucleic acid probes to nontarget nucleic acid sequences is still a major shortcoming when performing various hybridization techniques.

One use of molecular hybridization that has achieved prominence is in situ hybridization. abeled DNA or RNA that is complementary to specific sequences of DNA or RNA in a sample s prepared. Such complementary DNA or RNA is referred to as an oligonucleotide probe. In this assay, oligonucleotide probes are designed to anneal to specific target RNA such as mRNA, or particular native or integrated gene sequences in the DNA. Cells or tissue slices can be briefly exposed to heat or acid, which fixes the cell contents, including the nucleic acid, in place on a glass slide, filter, or other material. The fixed cell or tissue is then exposed to labeled complementary DNA or RNA probes for hybridization. Labeling agents may be radioisotopes such as $^{32}$P, fluorescent dyes, biotinylated nucleotide analogues, antigens or any other commonly performed labeling technique. After a period of incubation, unhybridized labeled DNA or RNA can be removed while the hybridized complexes are detected to reveal the presence and/or location of specific RNA or DNA within individual cells or tissue slices. Although this technique is popular, continued efforts are necessary to improve the sensitivity of the assay and to decrease non-specific binding (background) of labeled probes (Darnell et al., *Molecular Cell Biology*, Second Edition, 1990, Scientific American Books, Inc.).

Another hybridization technique that is commonly used in the art is the hybridization of labeled probes to immobilized nucleic acids. There are many methods available to hybridize labeled probes to nucleic acids that have been immobilized on solid supports such as nitrocellulose filters or nylon membranes. These methods differ in various respects, such as solvent and temperature used; volume of solvent and length of hybridization; degree and method of agitation; use of agents such as Denhardt's reagent or BLOTTO to block the nonspecific attachment of the probe to the surface of the solid matrix; concentration of the labeled probe and its specific activity; use of compounds, such as dextran sulfate or polyethylene glycol, that increases the rate of reassociation of nucleic acids; and stringency of washing following the hybridization.

In traditional assay methods, several different types of agents can be used to block the nonspecific attachment of the probe to the surface of the solid support. Such agents include Denhardt's reagent, heparin, nonfat dried milk, and the like. Frequently, these agents are used in combination with denatured, fragmented salmon sperm or yeast DNA and detergents such as SDS. Blocking agents are usually also included in both the prehybridization and hybridization solution when nitrocellulose filters are used. When nylon membranes are used to immobilize the nucleic acids, the blocking agents are often omitted from the hybridization solution, since high concentrations of protein are believed to interfere with the annealing of the probe to its target. In order to minimize background problems, it is best to hybridize for the shortest possible time using the minimum amount of probe, however, it is not always possible to eliminate all nonspecific binding of probes, particularly if the conditions are such that the detectable amount of nucleic acid is low (Sambrook et al., *Molecular Cloning, A Laboratory Manual*, Second Edition, 1989, Cold Spring Harbor Laboratory Press).

Nucleic acid hybridization is also the most reliable method for screening cDNA libraries for clones of interest. Large numbers of clones can be analyzed simultaneously and rapidly through the use of nucleic acid probes. Different techniques employ probes of varying length and specification. Homologous probes contain at least part of the exact nucleic acid sequence of the desired cDNA. They can be used in a variety of ways, such as, using a partial clone of an existing cDNA to isolate a full-length clone from a cDNA library. Hybridization with homologous probes is carried out under stringent conditions. Partially homologous probes are used to detect cDNA clones that are related but not identical to the probe sequence. For example, if the same gene has already been cloned from another species, or a related gene has been cloned from the same species, it can be experimentally determined whether the nucleic acid sequence has been sufficiently conserved to allow the screening of a cDNA library by hybridization. It is necessary to establish conditions that will allow the previously cloned gene to be used as a probe for the cDNA of interest, without undue interference from background hybridization resulting in non-specific signal generation. For more detailed information on hybridization assays and conditions, please see Sambrook et al. (supra).

There are several different agents that can be used to block non-specific binding of nucleic acid probes to surfaces in hybridization assays (supra). However, it is desirable to provide improved methods for the use of nucleic acid probes in hybridization techniques that increase the signal-to-noise ratio and decrease non-specific signal generation. The present invention addresses these needs.

SUMMARY OF THE INVENTION

The present invention relates to degradable nucleic acid probes and to assays and methods using these probes in the detection of target nucleic acid sequences in a sample. The purpose of the degradation process is to reduce non-specific signal generation.

An assay for detecting a target nucleic acid sequence, employing degradable probes is contemplated by the present invention. Preferably, the assay is a solution-based or an in situ nucleic acid hybridization assay using nucleic acid probes that are susceptible to chemical or enzymatic degradation. The assay comprises (1) hybridizing labeled, degradable nucleic acid probe(s) to a target sequence, creating a target-specific product from the probe(s), (2) degrading or separating the target-complementary region from the labeled region of the probe(s), and (3) detecting the presence of the labeled region.

One aspect of the present invention provides a method for detecting a target nucleic acid sequence in a sample whereby at least one pair of nucleic acid probes anneals to the target nucleic acid. The probes are characterized by two nucleic acid regions which form a terminal probe-probe branch or stem after the base pairing of the probes to the adjacent regions of the target nucleic acid sequence. The regions of the probe which are capable of forming the stem or probe-probe branch as described herein are also referred to as "stem regions" or "probe-probe regions". The probes have at least one crosslinking compound positioned within the stem region of at least one of the probes of the probe pair. The stem region of the second probe of the probe pair incorporates a reactant which is capable of forming a covalent bond with the crosslinking compound of the stem region of the first probe. Alternatively, both stem regions may incorporate a crosslinking compound, capable of forming a covalent bond by reaction of two crosslinking compounds, such as by dimerization. The covalent bond occurs after base pairing of the probes to the target nucleic acid sequence, and thereby permanently crosslinks the stem regions of the probe pair to each other. In addition, at least one of the stem regions of the probes contains a detectable moiety or signal-generating moiety bonded to the end of the stem region. The signal is generated and detected after the crosslinking of the stem which in turn occurs after base pairing of the probes to the target nucleic acid sequence. The nucleic acid probes are designed in a manner such that the target-specific hybridization region or target-complementary region of the probe can be separated via a degradation process from the detectable, labeled region. Hence, the remaining portion of the probes consists of the stem and the label. The purpose of this separation is to improve the signal-to-noise ratio by reducing background specific or non-specific signal generation.

Another aspect of the present invention provides nucleic acid probes that comprise a nucleic acid sequence that includes a modified or unmodified nucleic acid region designed to form a probe-probe branch or stem after base pairing of at least two probes to the adjacent regions of a target nucleic acid sequence. The regions of the probe that are capable of forming a stem are also referred to as "stem regions" or "probe-probe regions". At least one of the stem regions of the probes contains a detectable moiety, such as a label, bonded to the end of the stem region. In a preferred embodiment of the present invention, the stem region of a probe of a probe pair comprises modified or unmodified purine nucleosides or derivatives, such as modified or unmodified adenine residues and at least one crosslinking compound, while the stem region of the other probe of the probe pair comprises modified or unmodified pyrimidine nucleosides or derivatives that function as reactant for the crosslinking compound. One preferred reactant consists of modified or unmodified thymidine residues. The probes hybridize to adjacent regions of the target sequence and form a probe-probe branch or stem which comprises a three-arm junction. Consequently, after base pairing of the probes to adjacent regions of the target nucleic acid, the stem regions of the probe pair are crosslinked and the terminal stem or probe-probe branch is formed. The covalent crosslink can be induced by photoirradiation or other means. The crosslinked stem is then separated from the target complementary region and subsequently detected. The crosslinking compounds referred to herein are non-nucleosidic, stable, photoactive compounds that comprise coumarinyl derivatives. Examples of crosslinking compounds that react with crosslinking compound reactants such as modified or unmodified pyrimidine nucleosides or derivatives are coumarin derivatives including (1) 3-(7-coumarinyl) glycerol; (2) psoralen and its derivatives, such as 8-methoxypsoralen or 5-methoxypsoralen; (3) cis-benzodipyrone and its derivatives; (4) trans-benzodipyrone; and (5) compounds containing fused coumarin-cinnoline ring systems. All of these molecules contain the necessary crosslinking group located in the right orientation and at the right distance to crosslink with a nucleotide. In addition, all of these molecules are coumarin derivatives, in that all contain the basic coumarin ring system on which the remainder of the molecule is based.

In another embodiment of the present invention, the stem region of a probe pair comprises modified or unmodified purine and/or pyrimidine nucleosides or derivatives and a first crosslinking compound, while the stem region of the other probe of the probe pair comprises modified or unmodified purine and/or pyrimidine nucleosides or derivatives and a second crosslinking compound. After base pairing of the probes to adjacent regions of the target nucleic acid, the stem regions of the probe pair are crosslinked through the reaction (e.g. dimerization) of the crosslinking compounds upon photoirradiation, and the stem or probe-probe branch is formed. The crosslinking compounds referred to herein are non-nucleosidic, stable, photoactive compounds that comprise aryl olefin derivatives. The double bond of the aryl olefin is a photoactive group that covalently crosslinks to a suitable reactant, such as another aryl olefin derivative positioned in the opposite strand of the probe-probe branch. Accordingly, the double bond of the aryl olefin is located in the right orientation and the right distance to crosslink with a non-nucleosidic reactant in the opposite probe-probe region after base pairing of the probes to adjacent regions of the target nucleic acid.

In a particularly preferred embodiment of the invention, the target-specific hybridization region or target-complementary region of the probes is separated via a degradation process from the detectable, labeled region of the probes prior to detection. One objective of this invention is to maintain a covalent connection via the crosslink between the two probe ends that form the labeled probe-probe branch or stem, while removing any portion of the probes up to the site of the crosslink, especially the target-complementary region of the probes. In particular, the target-comlementary region of the probes is to be degraded or separated (e.g. cut away) from the stem of the probes. The methods for degradation or cutting include chemical and enzymatic means, wherein the method of choice depends upon the composition of the probes. The target-complementary region of the probes may comprise ribonucleotides, deoxyribonucleotides, or non-natural substitutes replacing a nucleotide unit(s) in the probes. Thus, the overall design of this system is to provide probes in which the stem region of the probe is resistant to the desired method of degradation or cutting used to separate or remove the target-complementary region of the probe. Following degradation, the separated and detectable portion of the probes consists of the stem and the label which is subsequently measured (vide infra) and quantified. The separation of the target-complementary region from the detectable region of the probes reduces non-specific binding of the probes and thereby improves the signal-to-noise ratio. As a result, background specific or non-specific signal generation is significantly reduced.

In another preferred embodiment of the instant invention, the stem regions of the probes contain a detectable moiety and a capture moiety which are bonded to the end of the stem regions. The detectable moiety may be any signal reporter group, and the capture moiety may be any capture group. In particular, the capture group and signal reporter group may be biotin and fluorescein, respectively. In an alternative embodiment, one or both stem regions of the probes contain detectable moieties which are bonded to the end of the stem regions. The detectable moieties may consist of labels such as fluorophores, radioisotopes, antigens, or enzymes. Furthermore, the labels may be designed such that it is the interaction between the two labels that generates a detectable signal.

In yet another preferred embodiment of the invention, the probes are selected from the roup consisting of SEQ ID NO. 1, SEQ ID NO. 2, SEQ ID NO. 3, SEQ ID NO. 4, SEQ ID NO. 5, SEQ ID NO. 6, SEQ ID NO. 7, and SEQ ID NO. 8.

The detection of target sequences, including but not limited to, full length genes, diagnostic marker genes, expressed sequence tags (ESTs), single nucleotide polymorphisms (SNPs), genomic DNA, cDNA, cccDNA, recombinant genes, and mRNA and rRNA are also encompassed by the present invention.

DETAILED DESCRIPTION OF THE INVENTION a) Definitions and General Parameters

The following definitions are set forth to illustrate and define the meaning and scope of specific terms used to describe the invention herein.

A "polynucleotide", "oligonucleotide", "nucleic acid", or "nucleic acid sequence" includes, but is not limited to, mRNA, cDNA, cccDNA, genomic DNA, and synthetic DNA and RNA sequences, comprising the natural nucleoside bases adenine, guanine, cytosine, thymine, and uracil, and also encompasses sequences having one or more modified or unmodified nucleosides. The term "nucleic acid" or "nucleic acid sequence" includes both oligonucleotides and polynucleotides. No limitation as to length or to synthetic origin are suggested by the use of either of these terms herein.

The term "target-specific hybridization region of a probe" or "target-complementary region of a probe" means a nucleic acid probe sequence which is capable of forming hydrogen bonds with another nucleic acid sequence, in particular a specific target sequence, under hybridization conditions, such as in buffered (pH. 7.0–7.5) aqueous, saline solutions (for instance, 1 mM to 2 M NaCl) at room temperature. Although hybridization conditions will depend on the length of the polynucleotides involved, typically they include the presence of at least one cation such as Na+, K+, Mg2+, or Ca2+, a near neutral pH, and temperatures less than 55° C. Although the sequences which hybridize to a polynucleotide may be about 90%–100% complementary to the polynucleotide, if the sequences are of sufficient length, in solutions with high salt concentrations, and/or under low temperature conditions, polynucleotides with complementarity of 70%, or even just 50%, may hybridize. Sequences which hybridize thereto typically comprise at least 10 nucleotides, and preferably at least about 15–30 nucleotides, and not more than about 1000 nucleotides, which are complementary to the target polynucleotide.

A "sample" as referred to in "a method for detecting a target nucleic acid sequence in a sample" may be a sample of tissue or body fluid, or an isolated sample. The term "tissue" is used herein to refer to any biological matter made up of one cell, multiple cells, an agglomeration of cells, or an entire organ. The term tissue, as used herein, encompasses a cell or cells which can be either normal or abnormal (i.e. a tumor). A "body fluid" may be any liquid substance extracted, excreted, or secreted from an organism or a tissue of an organism. The body fluid need not necessarily contain cells. Body fluids of relevance to the present invention include, but are not limited to, whole blood, serum, plasma, urine, cerebral spinal fluid, tears, and amniotic fluid. The term "isolated sample" means that the material comprising the sample has been removed from its original environment (e.g. the natural environment if it is naturally occurring). For example, naturally-occurring polynucleotides present in a living animal or tissue slice are not isolated, but the same polynucleotides could exist isolated in solution outside of their original environment, or be part of a vector or composition, and be isolated in that such vector or composition is not part of their original environment.

The term "detectable moiety" refers to any signal-generating moiety, signal reporter group, labeling agent, or label that is linked to a nucleic acid sequence or probe in order to assist in reporting or detecting a target nucleic acid of interest, such as DNA or RNA in a sample. The detectable moiety may be linked to one or more nucleic acid probes which function alone or in combination with each other. The detectable moiety may be directly detectable such as a radioisotope, fluorophore, or a direct enzyme label (e.g. enzyme conjugated directly to the probe); or indirectly detectable such as an antigen to which is then bound an enzyme-antibody conjugate which converts a substrate of the enzyme into a detectable product. Alternatively, fluorescein or any other detectable moiety may be used.

The term "capture moiety" or "capture group" as used herein is a moiety that works in combination with a detectable moiety, wherein one nucleic acid probe in a probe pair is labeled with a detectable moiety and the other probe in a probe pair is labeled with a capture moiety. The capture moiety may be any antigen, receptor substrate, or biotin, which causes the binding of the product onto a solid support containing, an antibody, a receptor, or avidin or streptavidin. The capture of the product occurs since the capture group is linked to the product. Depending on the moieties used, biotin would be bound to avidin or streptavidin, the antigen would be bound to the antibody, or the receptor substrate would be bound to the receptor.

The term "degradable probe" refers to a nucleic acid sequence or probe in which the detectable region of the probe may be separated from the target-complementary region of the probe by chemical or enzymatic means in order to improve the signal-to-noise ratio by reducing background specific or non-specific signal generation. The detectable and separable region of a pair of probes is also referred to as the probe-probe branch or stem. The probe-probe branch or stem consists of the portions of each probe which are not target-complementary but rather are designed to interact with one another (infra). Degradable probes can be used, for example, in an assay for nucleic acid detection such as a hybridization assay. Enzymatic means, as referred to herein, include but are not limited to enzymatic agents which have the ability to degrade DNA and/or RNA. Examples of enzymatic agents that degrade or cut deoxyribonucleotides are nucleases such as DNase I, micrococcal nuclease, Nuclease SI, or mung bean nuclease; or exnucleases such as exonuclease Ill. Examples of enzymatic agents that degrade or cut ribonucleotides are ribonucleases such as RNase A, S1, phosphodiesterase I, phosphodiesterase II, or RNase H. Chemical means, as referred to herein, include but are not limited to chemical agents that degrade RNA such as sodium hydroxide; or chemical agents that degrade DNA such as natural antibiotics (e.g. bleomycin, neocarzinostatin) or synthetic reagents (e.g. methidiumpropyl-EDTA iron (11) complexes).

The term "crosslinking compound" refers to a chemical compound that is positioned within a nucleotide sequence of a probe described herein. The crosslinking compound may be optionally positioned within the probe-probe region or stem region of one probe of a probe pair or probe set, wherein one probe may incorporate the crosslinking compound while the other probe may consist of one or more modified or unmodified purine or pyrimidine nucleoside(s) or derivative(s) which finction as reactant for the crosslinking compound. The crosslinking compound is designed to form a covalent bond with the reactant after base pairing of the probes to the target nucleic acid sequence. Alternatively, both stem regions incorporate a crosslinking compound, capable of forming a covalent bond upon reaction (e.g. dimerization), after base pairing of the probes to the target nucleic acid sequence. The crosslinking compounds contemplated by the present invention are discussed in detail in pending U.S. application Ser. No. 09/189,294; and U.S. Pat. Nos. 6,005,093; 5,082,934; and U.S. Pat. No. 30 4,826,967.

The terms "probe-probe branch" and "stem" are used interchangeably herein and describe a nucleic acid region of a probe pair that is to be photo-crosslinked after base pairing of the two probes to adjacent regions of a target nucleic acid sequence and subsequently separated from the target-specfic regions of each probe. The probe regions that are capable of forming the stem or probe-probe branch are referred to as "stem regions" or "probe-probe region". The stem regions first interact non-covalently through hydrogen bonding, salt bridges, and/or Van der Waal forces. The crosslinking of the stem then occurs after hybridization of the probe pair to the complementary target sequence. The crosslink is possible because the probes have at least one crosslinking compound positioned within one of the stem regions of the probe pair. The other stem region of the probe pair incorporates a reactant which forms a covalent bond with the crosslinking compound of the stem after base pairing of the probes to adjacent regions of the target nucleic acid. Alternatively, both stem regions incorporate a crosslinking compound, capable of forming a covalent bond upon photoreaction, (e.g. dimerization) after base pairing of the probes to the target nucleic acid sequence. The stem region of any probe exists in unhybridized form until the region of the probe that binds to the target has hybridized to the complementary target sequence. Hence, the stem region of any given probe may be indistinguishable from the rest of the probe until a stem has been formed. The terms probe-probe branch, stem, probe-probe region(s), and stem region(s) as claimed should not be unduly limited. No limitation as to size or length is suggested by the use of these terms. It will be apparent to those skilled in the art that variations of these terms are intended to be within the scope of the claims. For example, when DNA or RNA probes are used to detect RNA of interest, the resulting probe-probe branch or stem may not be separated as such that only the structure of the stem remains behind. Although, the target-complementary region will have been substantially degraded, several RNA bases of the target may remain attached to the stem which will not interfere with the purpose of the invention. Alternatively, when DNA or RNA probes are used to detect DNA of interest, the resulting probe-probe branch or stem may also not be separated as such that only the structure of the stem remains. Similarly, the target-complementary region will have been mostly degraded, but several DNA bases of the target may remain attached to the stem which will not interfere with the purpose of the invention. The same is true for conditions in which probes or targets are comprised of modified nucleic acids, nucleic acid derivatives, or nuclei acid analogs. The crosslinked probe-probe branch or stem may be separated from the target-complementary region and subsequently detected, regardless of length and size of the probe-probe branch or stem.

The term "N" is used to illustrate one or more modified or unmodified nucleic acid(s), nucleic acid derivative(s), or nucleic acid analogue(s). For example, probes comprising unmodified purine and/or pyrimidine nucleosides or derivatives are contemplated by the present invention, wherein N can be used to illustrate any number of such residues. Examples of unmodified residues are thymine or thymidine, cytosine, adenine, guanine, and uracil. Alternatively, probes comprising modified purine and/or pyrimidine nucleosides or derivatives are also contemplated by the present invention. Similarly, N can be used to depict any number of such modified residues. Examples of modified residues are deoxythymidine, deoxythymidine phosphate, 5-fluorouracil, and the like. No limitation as to size or length is suggested by the use of the term N. The term "N(a)" or "N(b)" is used to depict any number of modified or unmodified nucleic acid(s), nucleic acid derivative(s), or nucleic acid analogue(s), such as in a probe or target sequence. The subscripts "a" and "b" refer to any number of integers and thereby to any number of residue(s). For example, if a equals 0–20 (a=0–20) then the term N(a) equals anywhere from 0 to 20 modified or unmodified nucleic acid residue(s), nucleic acid derivative(s), or nucleic acid analogue(s). It will be obvious to someone skilled in the art that N(a) and N(b) are used to illustrate an approximate number of residue(s) in a probe or target sequence. Therefore, the terms N, N(a), and N(b) must not be unduly limited in size or length.

b) Hybridization Assay using Degradable Probes

The instant invention discloses solution-based and in situ nucleic acid hybridization assays using nucleic acid probes that are susceptible to chemical or enzymatic degradation. The purpose of the invention is to use the sequence-specific hybridization properties of nucleic acid probes to detect the presence of a target sequence, create a target-specific product from the probe(s), degrade or separate the target-complementary region of the probe(s), and detect the presence of the target specific product. The purpose of the degradation process is to improve the signal-to-noise ratio by reducing background specific or non-specific signal generation.

One aspect of the present invention provides a method for detecting a target nucleic acid sequence in a sample whereby at least one pair of nucleic acid probes anneals to the target nucleic acid. The method is performed by combining the target nucleic acid with the probes or probe pairs (vide infra) in an appropriate medium for base pairing. The nucleic acid may be DNA or RNA, single or double stranded, or other molecule which comprises pyrimidines and/or purines capable of base pairing.

In particular, one aspect of the present invention provides the degradable probes. The probes are characterized by nucleic acid regions which form a probe-probe branch or stem after the base pairing of at least two probes to the adjacent regions of the target nucleic acid sequence. Preferably, the nucleic acid probes comprise a nucleic acid sequence that includes a modified or unmodified nucleic acid region which is designed to form the probe-probe branch or stem after base pairing of at least two probes to the adjacent regions of the target nucleic acid sequence. The pair of probes is complementary to the target sequence except for the regions of the probes that form the stem. Each of the probes contains a stem region which does not bind to the target sequence. The stem regions exist in unhybridized form until the regions of the probe that bind the target nucleic acid have hybridized to the complementary target sequence. Consequently, the stem region of any given probe may be indistinguishable from the rest of the probe until a stem has been formed. The stem regions first interact non-covalently through hydrogen bonding, salt bridges, and/or Van der Waal forces. Then, after base pairing of the probes to adjacent regions of the target nucleic acid, the stem regions of the probe pair are crosslinked and the stem is formed. The crosslink is possible since the probes have at least one crosslinking compound positioned within one of the stem regions of the probe pair. The other stem region of the probe pair incorporates a reactant which forms a covalent bond with the crosslinking compound of the stem. Alternatively, both stem regions incorporate a crosslinking compound, capable of forming a covalent bond upon photoreaction (e.g. dimerization). After sufficient incubation, the probes hybridize to the target nucleic acid in the sample and the crosslinking system is activated resulting in covalent binding between the two probes. Hence, the covalent bond occurs after base pairing of the probes to the target nucleic acid sequence and thereby permanently crosslinks the stem regions to each other. The crosslinked stem is then separated from the target-complementary region and subsequently detected.

Each of the probes has a sequence length of at least 10 nucleotides, preferably about 15 to nucleotides and not more than about 1000 nucleotides, where the sequence is not less than 80 percent homologous to the target sequence, and more preferably 90–100 percent homologous to the target sequence. The base pairing regions present on the target nucleic acid will normally not be separated by more than about 10 nucleotides, more usually not more than about 5 nucleotides, and preferably not more than about 1 nucleotide. In a preferred embodiment of the invention, the probes are about 20 to 30 nucleotides in length and are about 95 percent homologous to the target wherein the base pairing regions present on the target nucleic acid are separated by about 1 nucleotide. It is understood that regardless of which probe pair is used to detect a given target sequence, the length of each probe within the pair of probes may vary. Each of the probes has a region that can form a stem or probe-probe branch with the other probe of the probe pair. After binding of the probes to the complementary target sequence, the crosslinking compound positioned within the stem of one of the stem regions of the probe pair is activated to form a covalent bond with the reactant positioned within the stem region of the other probe in the probe pair and thereby permanently crosslinks the stem regions of each member of the probe pair to each other. In addition, at least one of the probes in a probe pair contains a detectable moiety or a signal-generating moiety which is optionally bonded to the 5' or 3' end of its stem region. The signal is detected or generated after the crosslinking of the stem which in turn occurs after base pairing of the probes to the target nucleic acid sequence.

In a particularly preferred embodiment of the instant invention, the region of the probes which is complementary to a desired target nucleic acid sequence in a sample is removable from the detectable region of the probes. The nucleic acid probes are designed in a manner such that the target-specific hybridization region or target-complementary region of the probe can be separated from the detectable moiety or signal generating-moiety via the degradation process. After binding of the probes to the adjacent regions of the target nucleic acid sequence and the resulting crosslink within the stem, the target-complementary region of the probes can be removed via chemical or enzymatic degradation. Hence, the remaining portion of the probes consists of the stem and the signal which can be easily detected in the assay after the appropriate washing step (vide infra) has been completed. The purpose of this separation is to improve the signal-to-noise ratio by reducing background specific or non-specific signal generation. Standard hybridization assays are known in the art and a commonly experienced problem is the non-specific binding of nucleic acid materials to surfaces and the production of non-specific signal in the assay. By separating the signal generating moieties from the nucleic acid hybridization region, the non-specific signal can be minimized. The only remaining signal derives from the crosslinked probe stem and attached moiety or moieties which is directly proportional to the target sequence in any given sample.

One objective of this invention is to maintain a covalent connection via the crosslink between the two probe ends that form the labeled probe-probe branch or stem, while removing any portion of the probes up to the site of the crosslink, especially the target-complementary region of the probes. In particular, the target-complementary region of the probes is to be degraded or separated (e.g. cut away) from the stem region of the probes. The methods for degradation or cutting include chemical and enzymatic means, wherein the method of choice depends upon the composition of the probes. The target-complementary region of the probes may comprise ribonucleotides, deoxyribonucleotides, or non-natural substitutes replacing a nucleotide unit(s) in the probes. Consequently, degradation methods will depend on the type of probe that is used in the assay.

In one embodiment of the invention, deoxyribonucleotides comprise the target-complementary region of the probe, wherein many nucleases can be used singly or in combination to selectively degrade or cut the probe. Enzymes with endonuclease activity that hydrolyze double-stranded DNA, such as DNase I or micrococcal nuclease, may be used to degrade the target-complementary region of the probe directly following the crosslinking step. Enzymes with endonuclease activity that hydrolyze single-stranded DNA, such as Nuclease S1 or mung bean nuclease, may be used in the method after denaturation of any probe-target duplexes. Alternatively, two orientation-specific exonucleases may be used in combination to degrade the probes of a probe pair. For example, exonuclease III displays 3'->5' exonuclease activity on double stranded DNA, whereas bacteriophage lambda exonuclease displays 5'->3' exonuclease activity. The two nucleases may be introduced into the sample directly following the crosslinking step to effect the desired probe degradation reactions. Likewise, other exonucleases are known which require single stranded DNA as a substrate, and may require the sample to be denatured prior to introduction of the enzyme. Optionally, chemical DNA cleavage reagents may be used in the degradation of deoxyribonucleotides. Examples include the natural antibiotics bleomycin and neocarzinostatin, as well as synthetic reagents such as methidiumpropyl-EDTA iron(II) complexes.

In an alternative embodiment of the invention, ribonucleotides comprise the target-complementary region of the probe, wherein chemical means such as strongly basic solutions may be used to degrade or cut the probe. Typically, sodium hydroxide solutions of concentration 0.1 M to 5M, are contacted with the probes, and the resulting solution may be incubated at room temperature or at higher temperatures, e.g. 30–90° C. The basic solution will cause the formation of nicks in the probe strand at the RNA base positions, wherein the time period needed for the reaction is dependant on both the concentration of hydroxide ion and the temperature of the incubation. Many enzymatic means can also be used to effect probe degradation or cutting at ribonucleotide sites. Enzymes known to cleave single stranded RNA include for example ribonuclease A, S1, phosphodiesterase I, phosphodiesterase II. Where the enzyme selectively acts upon single stranded RNA, the solution may need to be brought to denaturing conditions (e.g. heated to a temperature above the melting temperature of the duplex) whereby the crosslinked probe-target duplex is separated from the target strand prior to initiation of the enzymatic process. Enzymes with endonuclease activity, such as RNase A and S1, may be used individually to effect the desired probe degradation reaction in each probe of the probe set. Enzymes with only orientation-dependent exonuclease activity are preferably used in pairs in order to effect the desired probe degradation reaction in each probe. For example, phosphodiesterase I displays 5'->3' exonuclease activity and phosphodiesterase II displays 3'->5' activity. The two enzymes would preferably be used in combination to degrade both probes of a set because one probe terminates with a 5' end in its target-complementary region whereas the other probe terminates with a 3' end in its target-complementary region. Alternatively, RNase H may be used to selectively degrade the RNA portion of a probe. RNase H displays RNA hydrolysis activity on RNA/DNA duplexes. In this case, probes with the target-complementary region comprising ribonucleotides are applied to the detection of DNA targets. After the probes have been contacted with the sample and allowed to hybridize and crosslink, RNase H may be introduced to effect the selective hydrolysis of the ribonucleotide units of the probes that are hybridized to the DNA target.

The stem is designed so that the structure beyond the crosslink site is not accessible to or recognizable by the enzyme or chemical agent and therefore not cut or degraded. This may be accomplished with or without modification of the sugar phosphate backbone of the probe nucleic acid sequence. The stem region of the probe may comprise ribonucleotides, deoxyribonucleotides, derivatives of ribonucleotides or deoxyribonucleotides, or non-nucleic acid components. The type of nucleic acid or non-nucleic acid moiety used in the stem is selected from any of the above groups that are not susceptible to the reagent to be used to degrade the target-complementary region of the probe. For example, when DNA nucleases are used for the degradation process, the stem portion of the probe may comprise ribonucleotides. Conversely, when RNA nucleases are used for the degradation process, the stem portion may comprise deoxyribonucleotides. Some nucleases however are known to hydrolyze both DNA and RNA substrates, such as S1, and phosphodiesterase I and II, in which case nuclease-resistant derivatives of the natural nucleotides or non-nucleic acid components are required. Many chemical modifications of the natural nucleotide structure are known to confer nuclease resistance to the moiety. For example, exchanging a sulfur atom for an oxygen atom in the phosphate moiety to create a thiophosphate moiety typically retards or halts the enzymatic hydrolysis reaction. Likewise replacing the phosphate group with a methyl phosphonate group confers enzymatic resistance. Non-natural linkages are also not recognized by enzymes and provide a useful means for constructing the stem portion of the probe. For example, peptide linkages are known to serve as a backbone moiety in nucleic acid structures that preserve the capability of base pair formation in complementary duplexes, but they have a non-natural backbone not recognized by any enzyme.

The present invention also encompasses naturally occurring nucleic acid moieties that may be used in the stem region of the probes between the crosslinker and any label at the probe terminus, or between the crosslinking site and any label at the probe terminus, regardless of the type of degradation method used. Where the number of natural bases between the crosslinker or crosslink site and the labeled probe terminus is fewer than 10, more preferably fewer than 3, the activity of a nuclease is significantly retarded because the crosslink and the label moieties alter the recognition site of the enzyme.

For stem formation to occur, each stem region of a probe which comprises one-half of the stem may include at least 2 or 3 paired nucleotides, and usually not more than about 20 base pairs. In a preferred embodiment, the nucleotide pairs will be A and T, where the nucleotides may be the same in one stem region or different, that is all T's in one stem region and all A's in the other stem region, or a mixture of A's and T's in the two stem regions of the probe pair. Alternatively, G and C may be used by themselves or in combination with A and T. Most preferably, the stem consists of 3 nucleotide units wherein one stem region is comprised of T's, and the other stem region is comprised of two A's and one crosslinking compound; or wherein one stem region is comprised of two T's and one crosslinking compound, and the other stem is comprised of two A's and one crosslinking compound. It is understood, that the particular choice of nucleotide will depend on the desired affinity, ease of synthesis, interaction with the covalent cross-linking compound, type of degradation method, and the like.

In a preferred embodiment of the instant invention, the stem regions of the probes contain a detectable moiety and a capture moiety which are bonded to the end of the stem regions. The detectable moiety may be any signal reporter group, and the capture moiety may be any capture group. In particular, the capture group and signal reporter group may be biotin and fluorescein, respectively. In an alternative embodiment, both stem regions of the probes contain detectable moieties which are bonded to the end of the stem regions. The detectable moieties may consist of labels such as fluorophores, radioisotopes, antigens, or enzymes. In an alternative embodiment, both stem regions of the probes contain moieties which in combination interact to provide a detectable signal, such as fluorescent resonance energy transfer pairs or activator/receptor pairs.

In another preferred embodiment, the stem region of a probe of a probe pair comprises modified or unmodified purine nucleosides or derivatives, such as modified or unmodified adenosine residues and at least one crosslinking compound, while the stem region of the other probe of the probe pair comprises modified or unmodified pyrimidine nucleosides or derivatives that function as a reactant for the crosslinking compound. One preferred reactant consists of modified or unmodified thymidine residues. The probes hybridize to adjacent regions of the target sequence and form a probe-probe branch or stem which comprises a three-arm junction. Consequently, after base pairing of the probes to adjacent regions of the target nucleic acid, the stem regions of the probe pair are crosslinked and the stem or probe-probe branch is formed. The covalent crosslink can be induced by photoirradiation or other means. Additionally, the covalent crosslink may cause the label to be activated and the probes become detectable. The crosslinked stem is then separated from the target complementary region and subsequently detected. The crosslinking compounds referred to herein are non-nucleosidic, stable, photoactive compounds that comprise coumarinyl derivatives. The coumarinyl derivatives are prepared by linking the phenyl ring of a coumarin molecule or derivative to a hydroxy or polyhydroxy hydrocarbon molecule, such as one of the terminal hydroxy groups of a glycerol molecule. The (poly)hydroxy hydrocarbon moiety of the resulting compound is equivalent to the sugar of a nucleoside, while the coumarin moiety occupies the position of a base. Accordingly, the compounds can be inserted into polynucleotide regions. The double bond between the 3 and 4 positions of the coumarin ring system is a photoactive group that forms a covalent crosslink to nucleosides in the opposite strand comprising the probe-probe region after base pairing of the probes of a probe pair to adjacent regions of the target nucleic acid. Examples of crosslinking compounds that react with crosslinking compound reactants such as modified or unmodified pyrimidine nucleosides or derivatives are coumarin derivatives including (1) 3-(7-coumarinyl) glycerol; (2) psoralen and its derivatives, such as 8-methoxypsoralen or 5-methoxypsoralen; (3) cis-benzodipyrone and its derivatives; (4) trans-benzodipyrone; and (5) compounds containing fused coumarin-cinnoline ring systems. All of these molecules contain the necessary crosslinking group (an activated double bond) located in the right orientation and at the right distance to crosslink with a nucleotide. In addition, all of these molecules are coumarin derivatives, in that all contain the basic coumarin (benzopyrone) ring system on which the remainder of the molecule is based. These crosslinking compounds are discussed in detail in U.S. Pat. No. 6,005,093.

In another embodiment of the present invention, the stem region of a probe of a probe pair comprises modified or unmodified purine and/or pyrimidine nucleosides or derivatives and a first crosslinking compound, while the stem region of the other probe of the probe pair comprises modified or unmodified purine and/or pyrimidine nucleosides or derivatives and a second crosslinking compound. After base pairing of the probes to adjacent regions of the target nucleic acid, the stem regions of the probe pair are crosslinked through the reaction (e.g. dimerization). of the crosslinking compounds upon photoirradiation, and the covalently joined stem or probe-probe branch is formed. The crosslinking compounds referred to herein are non-nucleosidic, stable, photoactive compounds that comprise aryl olefin derivatives. The aryl olefm derivatives are prepared by linking the aryl moiety to a functionlized saturated or unsaturated hydrocarbon molecule, such as glycerol. The functionalized hydrocarbon moiety of the resulting compound is equivalent to the sugar of a nucleoside, while the aryl olefin moiety occupies the position of a base. Accordingly, the compounds can be inserted into polynucleotides. The double bond of the aryl olefin is a photoactive group that covalently crosslinks to a suitable reactant, such as another aryl olefin derivative positioned in the opposite strand of the probe-probe branch. The double bond of the aryl olefin is located in the right orientation and the right distance to crosslink with a non-nucleosidic reactant in the opposite probe-probe region after base pairing of the probes to adjacent regions of the target nucleic acid and subsequent photoirradiation. These crosslinking compounds are discussed in detail in pending U.S. application Ser. No. 09/189,294.

In yet another preferred embodiment of the invention, the probes are selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, and SEQ ID NO. 8.

The detection of target sequences, including but not limited to, full length genes, diagnostic marker genes, expressed sequence tags (ESTs), single nucleotide polymorphisms (SNPs), genomic DNA, cDNA, cccDNA, recombinant genes, and mRNA and rRNA is also encompassed by the present invention. The target sequences may be double stranded or single stranded. Furthermore, they may be naturally occurring or artificial in nature. Target sequences may be purified or unpurified, exist in solution or within a fluid or tissue.

The instant invention encompasses nucleic acid probes that are susceptible to chemical and enzymatic degradation, and methods of using such probes in the detection of target nucleic acid sequences. The overall design of this system is to provide probes in which the stem region of the probe is resistant to the desired method of degradation or cutting used to separate the target-complementary region of the probe from the labeled region of the probe. Following degradation, the separated and detectable region of the probes consists of the stem and the label which is subsequently measured (vide infra) and quantified. The separation of the target-complementary region from the detectable region of the probes reduces non-specific binding of the probes and thereby improves the signal-to-noise ratio. As a result, background specific or non-specific signal generation is significantly reduced.

c) Protocol

The following protocol illustrates the invention wherein two DNA probes crosslink within a probe-probe branch or stem and a restriction endonuclease functions as the degradation agent.

Probes*:

1. Combine probes in a sample solution (containing target)

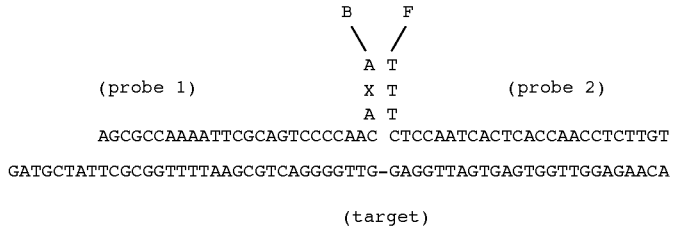

(target)

2. Crosslink the two probes together

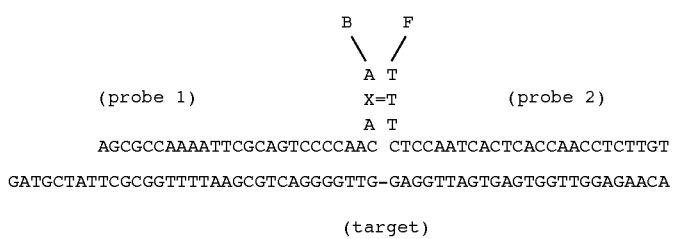

(target)

3. Use endonuclease restriction enzyme to degrade the probes (and other nucleic acid material)

The hyphen in the target sequences merely serves to preserve the alignment of the bases in the two strands; the two bases flanking the hyphen are joined by a normal phosphodiester linkage.

B represents biotin

F represents Fluorescein

X represents a crosslinking compound

The '=' between the X and the T represents a covalent crosslink.

The stem is designed so that the structure beyond the crosslink site is not accessible to or recognizable by the enzyme and therefore not cut by the enzyme. This may be accomplished without modification, or with modification of the sugar phosphate backbone (for example phosphorothioate, methyl phosphonate, peptide link, and the like).

The portion of the probes that remains now consists of the two linked labels, which in this embodiment is a biotin group and a fluorescein group, or respectively, a capture group and a signal reporter group. Alternatively, the two labels may be fluorophores that may interact to provide a signal by fluorescence resonance energy transfer. The assay may proceed with the capture of the capture group which is linked to the labeled stem onto a solid support, followed by wash steps to remove unbound materials and probes (probe digests) from the vicinity, and then steps to detect the presence of the signal reporter group (see Detection Methods, infra). The stem is. retained since the capture group, such as biotin, is linked to the stem. In this embodiment, biotin is bound to avidin or streptavidin coated beads.

Several variations of this particular embodiment are also disclosed herein (supra).

For RNA Probes

Use RNase A as the enzymatic agent for probe degradation.

Use sodium hydroxide as a chemical agent for probe degradation.

For DNA Probes

Use DNase I as the enzymatic agent for probe degradation.

Use an endonuclease as the enzymatic agent for probe degradation (i.e. micrococcal nuclease).

The following exemplifies the invention using the probes of Table 1. Sets of DNA probes are tested for their ability to hybridize to nucleic acid sequences of interest and to be detected via a labeled moiety. Degraded and non-degraded probes are compared.

TABLE 1

Probe Sequences.

| | | |
|---|---|---|
| Probe 1 | 5'-TCTGCCGATCCATACTGCGGAACAXAB | SEQ ID NO. 1 |
| Probe 2 | 5'-FP*TTTTCCTAGCMGCTTGTTTTGCTCGC | SEQ ID NO. 2 |
| Probe 3 | 5'-TATATGGATGATGTGGTATTGGAXAB | SEQ ID NO. 3 |
| Probe 4 | 5'-FP*TTTGGGCCAAGTCTGTACARCATC | SEQ ID NO. 4 |
| Probe 5 | 5'-CATTTGTTCAGTGGTTCGYAGGGCAXAB | SEQ ID NO. 5 |
| Probe 6 | 5'-FP*TTTTTTCCCCCACTGTTTGGCTTTCAG | SEQ ID NO. 6 |
| Probe 7 | 5'-CAGAGTCTAGACTCGTGGTGGACAXAB | SEQ ID NO. 7 |
| Probe 8 | 5'-FP*TTTTTCTCTCAATTTTCTAGGG | SEQ ID NO. 8 |

*= phosphorothioate diester (instead of the normal phosphodiester)
X = 3-(7-coumarinyl) glycerol
P = tetraethylene glycol
B = biotin TEG (Glen Research)
F = fluorescein phosphoramidite (Cruachem)
M = A and C
Y = C and T Sample Protocol Samples were prepared by combining a lysis solution (119.2 μl), probe solution (36.4 μl) and neutralization solution (44.4 μl) together in the wells of a 96-well microtiter plate.

The lysis solution was 0.1875 M sodium hydroxide. Two types of lysis solution were prepared. One contained only the sodium hydroxide, the other also contained 24 fmol of a plasmid vector containing the hepatitis B viral genome. These solutions were boiled for 30 minutes. The resulting lysates were filtered through an Acrodisk 0.45 μlm syringe filter prior to distribution into the plate wells.

In the probe solution the concentration of the crosslinker probe (Table 1: probe 1, 3, 5 or 7) was 54.9 nM, and the concentration of the reactant probe (Table 1: probe 2, 4, 6 or 8) was 137.4 nM. The probe solution also contained 0.012% bovine serum albumin, 1.815 M sodium chloride, and 0.001% phenol red as a pH indicator.

The neutralization solution was 0.15 M citric acid, 0.31 M sodium dihydrogen phosphate, 1.5 M sodium chloride, 0.42% Tween 20 and 35% formamide.

After combining all the reagents, the plate was incubated for 15 minutes at 400° C., and hen photoirradiated by a bank of five 8 W bulbs (F8T5/350BL, Sylvania) at 300–370 nm hrough a 1.5 mm Pyrex filter for 30 minutes while maintaining the incubation temperature of 0° C.

Streptavidin-coated paramagnetic beads (75 g, Dynal M280) were added to each well, and incubated at room temperature for 30 minutes.

In each of the following wash steps, the microtiter plate was first placed on a magnetic plate to collect the paramagnetic beads into a pellet, the liquid was removed by aspiration, and a new solution was added to the well, resuspending the paramagnetic beads in the process.

First, the samples were washed with 100 μl of Wash I (50 mM sodium hydroxide and 0.1% sodium dodecyl sulfate). Next, the samples were washed once with 200 μl of Wash II (1×SSC and 0.1% Tween 20).

The samples were then subjected to two incubations with differing combinations of restriction enzyme and antibody conjugate treatment. The combinations used are summarized in Table 2. The same buffer solution was used in all instances, and a restriction enzyme, monococcal nuclease, and an antibody conjugate, anti-fluorescein/alkaline phosphatase, were either omitted, included separately, or included together in the incubations.

The buffer solution was 0.1 M Tris (pH 7.5), 0.1125 M sodium chloride, 0.5×SSC, 1.0 mM magnesium chloride, 1.0 mM calcium chloride, 0.1% Tween 20 and 0.25% bovine serum albumin. The amount of micrococcal nuclease used was 1 unit. The anti-fluorescein/alkaline phosphatase was used as a 1/20,000 dilution.

In the first incubation, 50 μl of the appropriate buffer was added to the wells and incubated for 30 minutes at 37° C. The samples were then washed two times with 220 μl of Wash II. Then, in the second incubation, again 50 μl of the appropriate buffer was added to the wells and incubated for 30 minutes at 37° C.

The samples were then washed four times with 220 μl of Wash II. Finally the wash solution was replaced with 100 μl of Attophos™. The substrate was incubated for 1 hour at 37° C., and the fluorescent signal was measured in a plate reading fluorometer (Packard Instruments).

Detection Methods

I. Label One Probe with a Detectable Moiety and Use the Following Detection Methods 1. Homogeneous detection by fluorescence polarization spectroscopy.
2. Mass spectroscopy (MALDI, TOF, Electrospray, etc.).
3. Separation of the product by mass or charge (i.e. chromatography or electrophoresis) followed by fluorescence detection, mass spectroscopy, catalyzed reporter deposition, etc.

II. Label each Probe with a Member of an Interacting Pair and Use the Following Detection Methods 1. Fluorescence resonance energy transfer.
2. LOCI method III. Label one Probe with a Detectable Moiety, and the Other Probe With a Capturable Moiety and Use the Following Detection Methods 1. The capture moiety may be, e.g. biotin, an antigen, or a receptor substrate which would each separately bring about the binding of the product onto a solid support containing, e.g. avidin or streptavidin, the antibody, or the receptor. The detectable moiety may be directly detectable, e.g. a fluorophore, radioisotope, or a direct enzyme label (e.g. enzyme conjugated directly to the probe) or indirectly detectable, such as an antigen to which is then bound an enzyme-antibody conjugate which converts a substrate of the enzyme into a detectable product.

Probe Pairs

Two probes comprise a probe pair. In Table 1 (supra), the following pairings comprise four probe pairs: (1,2), (3,4), (5,6), and (7,8).

The probe pairs were designed such that the two probes hybridized to adjacent regions of the target, and in doing so formed a probe-probe branch or stem which comprised a three-arm junction. In the probe-probe branch or stem of the three-arm junction, one probe had a crosslinking compound and a biotin label, and the other probe consisted of thymidine bases reactant for the crosslinking compound), a phosphorothioate linkage between the last thymidine and the tetraethylene glycol spacer unit, and a fluorescein moiety.

Each probe pair was tested in three ways, each in the presence and absence of the target DNA:

(1) No enzymatic digestion.
(2) Enzymatic digestion with antibody binding after the digestion.
(3) Enzymatic digestion with antibody binding during the digestion.

Tables 2 and 3 below illustrate the conditions under which the probes were tested.

TABLE 2

The six conditions (A–F) used to test each probe pair are summarized below.

| Condition | A | B | C | D | E | F |
| --- | --- | --- | --- | --- | --- | --- |
| Target DNA | no | yes | no | yes | no | yes |
| Incubation 1 | buffer | buffer | enzyme | enzyme | buffer | buffer |
| Incubation 2 | Ab | Ab | Ab | Ab | enzyme/Ab | enzyme/Ab |

TABLE 3

Results.
Signal: Relative Fluorescent Units

| Probe Set | Condition | | | | | |
| --- | --- | --- | --- | --- | --- | --- |
| | A | B | C | D | E | F |
| (1, 2) | 108 | 910 | 33 | 2199 | 31 | 2026 |
| (3, 4) | 69 | 523 | 29 | 1929 | 30 | 1535 |
| (5, 6) | 124 | 896 | 38 | 2114 | 34 | 1708 |
| (7, 8) | 42 | 1066 | 25 | 1546 | 24 | 1591 |

For all of the four probe pairs, similar results were observed. The non-specific signal from negative samples was reduced (C and E compared to control A), and the target-specific signal was greater in the samples treated to degrade the probes (D and F compared to control B).

Comparing the signals observed in the absence of target DNA (conditions A, C, E), samples treated with the restriction endonuclease (C, E) yielded signals that were both lower and more uniform (C: average: 31.25;%CV: 17.8.; E: average: 29.75;%CV: 14.1). In contrast, the signals in the untreated samples were higher and varied considerably (average: 85.75;%CV: 42.4). Enzymatic digestion of the samples yielded lower non-specific ("background") signals in the negative samples.

Comparing the signals observed in the presence of target DNA (conditions B, D, F), samples treated with the restriction endonuclease yielded signals that are 50–300% greater than the signal obtained from the untreated samples. The greater signal may be posited to be due to the significant reduction in size and charge of the detectable product as a result of the enzymatic degradation process, thus providing a more favorable binding partner for the antibody conjugate or a more favorable environment for the subsequent enzymatic reaction to generate the detectable fluorescent product.

All patents, patent applications, and publications referred to herein are incorporated by reference into this application.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for detecting a target nucleic acid sequence in a sample, comprising:
   (i) combining a sample with a pair of probes under conditions of sequence-specific hybridization, wherein each probe has a target-complementary region capable of base paring to a portion of the target nucleic acid sequence and a probe-probe branch-forming region at either terminus not complementary to said target nucleic acid sequence at a terminus of the probe that is capable of forming via interaction with the other probe a probe-probe branch, at least one crosslinking compound positioned within the probe-probe branch-forming region of one probe which forms a covalent crosslink with a crosslinking compound reactant positioned within the probe-probe branch-forming region of the other probe of the probe pair after base pairing of the probes to said target nucleic acid sequence, and at least one detectable moiety bonded to at least one of the probes;
   (ii) photoirradiating said sample to crosslink the probe-probe branch-forming region of adjacent pairs of probes;
   (iii) separating the crosslinked probe-probe branch-forming region of the probes from the target complementary region by degrading the target-complementary region and the target nucleic acid sequence that is base paired to the target-complementary region; and
   (iv) detecting the presence of at least one separated, crosslinked probe-probe branch as indicative of the presence of said target nucleic acid sequence in said sample.

2. A method of claim 1, wherein the crosslinking compound is selected from the group consisting of coumarin, coumarin derivatives, 3-(7-coumarinyl) glycerol; psoralen, psoralen derivatives, 8-methoxypsoralen, 5-methoxypsoralen; cis-benzodipyrone, cis-benzodipytrone derivatives; trans-benzodipyrone, trans-benzodipyrone derivatives; and compounds containing fused coumarin-cinnoline ring systems.

3. A method of claim 1, wherein the crosslinking compound reactant is selected from the group consisting of pyrimidines and pyrimidine derivatives.

4. A method of claim 1, wherein the detectable moiety is selected from the group consisting of fluorescein, fluorophore, radioisotope, antigen, or enzyme.

5. A method of claim 1, wherein the pair of probes is comprised of ribonucleic acid.

6. A method of claim 1, wherein the pair of probes is comprised of deoxyribonucleic acid.

7. A method of claim 1, wherein the probe-probe branch-forming region of each probe of a probe pair comprises at least two nucleotides which form base pairs.

8. A method of claim 1, wherein the probe-probe branch-forming region of each probe of a probe pair has from about 2 to about 8 nucleotides.

9. A method of claim 1, wherein the probes are selected from the group consisiting of SEQ ID NO. 1, SEQ ID NO. 2, SEQ ID NO. 3, SEQ ID NO. 4, SEQ ID NO. 5, SEQ ID NO. 6, SEQ ID NO. 7, and SEQ ID NO. 8.

10. A method of claim 1, wherein separating the crosslinked probe-probe branch of the probes from the target-complementary region is accomplished through chemical or enzymatic degradation.

11. A method of claim 1, wherein said target nucleic acid sequence is single stranded or double stranded deoxyribonucleic acid.

12. A method of claim 1, wherein said target nucleic acid sequence is ribonucleic acid.

13. A method of claim 1, wherein said target nucleic acid sequence has a gap of no more than about two nucleotides between the sequences homologous to the pair of probes.

14. A method for detecting a target nucleic acid sequence in a sample, comprising:
   (i) combining a sample with a pair of probes under conditions of sequence-specific hybridization, wherein each probe has a probe-probe branch-forming region at either terminus not complementary to said target nucleic acid sequence that is capable of forming via interaction with the other probe a probe-probe branch, at least one crosslinking compound positioned within the probe-probe branch-froming region of one probe which forms a covalent crosslink with a crosslinking compound reactant positioned within the probe-probe branch-forming region of the other probe of the probe pair after base pairing of the probes to said target nucleic acid sequence, at least one signal reporter group bonded to one probe, and at least one capture group bonded to the other probe;
   (ii) photoirradiating said sample to crosslink the probe-probe branch-forming region of adjacent pairs of probes;
   (iii) separating the crosslinked probe-probe branch-forming region of the probes from a target-complementary region; and
   (iv) detecting the presence of at least one separated cross-linked probe-probe branch, as indicative of the presence of said target nucleic acid sequence in said sample.

15. A method of claim 14, wherein the signal reporter group is selected from the group consisiting of fluorescein, fluorophore, radioisotope, antigen, and enzyme.

16. A method of claim 14, wherein the capture group is selected from the group consisting of biotin, an antigen, and a receptor substrate.

17. A method of claim 14, wherein the crosslinking compound is selected from the group consisting of coumarin, coumarin derivatives, 3-(7-coumarinyl) glycerol; psoralen, psoralen derivatives, 8-methoxypsoralen, 5-methoxypsoralen; cis-benzodipyrone, cis-benzodipyrone derivatives; trans-benzodipytrone, trans-benzodipyrone derivatives; and compounds containing fused coumarin-cinnoline ring systems.

18. A method of claim 14, wherein the crosslinking compound reactant is selected from the group consisiting of pyrimidines and pyrimidine derivatives.

19. The method of claim 1, wherein the crosslinking compound reactant comprises a crosslinking compound, such that a first crosslinking compound positioned within the probe-probe branch-forming region of the first probe of the probe pair is capable of forming a crosslink with a second crosslinking compound positioned within the probe-probe branch-forming region of the second probe of the probe pair.

20. The method of claim 19, wherein the crosslinking compounds are selected from the group consisting of aryl olefins and aryl olefin derivatives.

21. The method of claim 14, wherein the crosslinking compound reactant comprises a crosslinking compound, such that a first crosslinking compound positioned within the probe-probe branch-forming region of the first probe of the probe pair is capable of forming a crosslink with a second crosslinking compound positioned within the probe-probe branch-forming region of the second probe of the probe pair.

* * * * *